United States Patent [19]
Coleman et al.

[11] Patent Number: 5,798,518
[45] Date of Patent: Aug. 25, 1998

[54] MEDICAL LASER CALIBRATION SYSTEM AND METHOD

[75] Inventors: Tony D. Coleman, San Jose; Scott A. Davenport, Half Moon Bay, both of Calif.

[73] Assignee: Laserscope, San Jose, Calif.

[21] Appl. No.: 508,518

[22] Filed: Jul. 28, 1995

[51] Int. Cl.$^6$ .............................. G01J 1/32; A61B 17/36
[52] U.S. Cl. ............... 250/205; 250/227.11; 128/303.1
[58] Field of Search ......................... 250/205, 227.11; 606/10–12, 15, 16; 607/88, 89, 93; 128/303.1

[56] References Cited

U.S. PATENT DOCUMENTS 4,800,877  1/1989  Losch .............................. 128/303.1

*Primary Examiner*—Stephone B. Allen
*Attorney, Agent, or Firm*—Heller, Ehrman, White & McAuliffe; Jacques M. Dulin, Esq.; Robert F. Dennis, Esq.

[57] ABSTRACT

A fiber optics calibration system (10) incorporated into a laser surgical system (12). A laser light source (14) produces a light beam (16), a portion of which is directed by a first beam splitter (18) into a radiation detector (26) and a further portion of which is directed by a safety detector (28) into a safety detector. A safety shutter (31) is interposed between the radiation detector (26) and the safety detector (28) and controlled by the safety detector (28). During calibration, the light beam is directed through a fiber optic cable (24) and then through a calibration adaptor (34) and calibration receptacle (36) a via a light pipe (38) to the safety detector (28). A calibration switch (40) locks out operation of the safety shutter (31) such that readings of the radiation detector (26) can be compared to those of the safety detector (28) and compensation from an expected standard value be made therefor by a controlling computer (42). In a preferred embodiment, the proximal end of the fiber or delivery device is a signature connector (23) which is uniquely recognized by the output port (22) as the proper fiber for the laser console (12). The calibration adaptor (34) is preferably adapted with appropriate internal and external contours to be complementary to the laser light output tip (33) of the fiber and to the internal contour (35) of the calibration receiver port (36). These features insure the correct fiber is employed with the console for which it was designed and helps prevent reuse of FDA cleared "single use only" fibers and delivery devices.

17 Claims, 2 Drawing Sheets

MEDICAL LASER CALIBRATION SYSTEM AND METHOD

DESCRIPTION

1. Technical Field

The present invention relates generally to the field of lasers, and more particularly to an improved method and means for calibrating the fiber optic transmission member used for the conduction of laser light, typically from a laser console to or through a delivery device, probe or fiber to the target.

2. Background Art

Where it is necessary to deliver a precise quantity of energy by means of a laser, as in laser surgery applications, it is important, if not critical, to calibrate the optical fiber to insure the accurate delivery of laser light energy to the target. Such calibration is intended to accurately compensate for losses through the fiber optic transmission means. As an example, U.S. Pat. No. 4,580,557 issued to Hertzmann teaches a method and means for accomplishing calibration to account for variables such as changes in peripheral (delivery) devices and/or changes over time or usage in such peripheral devices and light transmission means.

The predominant current method for calibrating such fiber optics is to measure the laser light prior to the proximal end of the fiber and then to compare that measurement with an external detector at the distal end. These two measurements are then used, by software in a controlling computer device, to produce a calibration factor. This method uses three detectors: the detector at the proximal end of the fiber optics (a "safety" detector), the external detector at the distal end of the fiber optics (a "calibration pod"), and a third ("radiation" or "surgical") detector which is to create a consistent base line prior to the proximal end of the fiber optic conductor.

Since light detectors are relatively expensive, and since such light detectors are themselves a potential source of inaccuracy and/or malfunction, such a plurality of detectors has been used only because it has been thought to be necessary to do so in order to achieve the desired result. To the inventors, knowledge, prior to the present invention, no means has existed in the art for accurately calibrating laser fiber optic conduction means without providing separate sensors at each end of the fiber optic conductor.

DISCLOSURE OF INVENTION—OBJECTS, SUMMARY AND ADVANTAGES

Accordingly, it is an object of the present invention to provide a method and means for accurately calibrating fiber optic conductors.

It is still another object of the present invention to provide a method and means for calibrating fiber optic conductors which is inexpensive to produce and to use.

It is yet another object of the present invention to provide a method and means for calibrating fiber optic conductors which is reliable in operation.

It is still another object of the present invention to provide a method and means for calibrating fiber optic conductors which can be adapted to existing and future laser devices.

Briefly, the preferred embodiment of the present invention is a laser calibration device incorporating an inexpensive acrylic light pipe. Laser light is detected prior to the proximal end of a fiber optic system (as in the prior art), before the light is transmitted through the optical fiber. Unlike in the prior art, at the distal end of the optical fiber, a light pipe is provided for returning light to the system safety detector such that the system has only two sensors: a radiation detector for setting up a baseline and determining the intensity of the laser light prior to the proximal end of the fiber optic transmission means, and the safety detector for detecting the light provided to the optical fiber and the light returned through the light pipe. The two signals (from the radiation detector and from the safety detector) are analyzed by software in the controlling computer to determine a calibration factor.

An advantage of the present invention is it reduces the cost of laser systems.

A further advantage of the present invention is that laser systems are made less complex.

Yet another advantageous the present invention is that it is readily implemented in existing and future laser systems.

Still another advantage of the present invention is that it provides more accurate calibration than prior art laser systems in at least some applications.

Yet another advantage of the present invention is that it is easy to use, requiring no specific separate calibration operation by the operator.

These and other objects and advantages of the present invention will become clear to those skilled in the art in view of the description of the best presently known mode of carrying out the invention and the industrial applicability of the preferred embodiment as described herein and as illustrated in the several figures of the drawing.

BEST MODE FOR CARRYING OUT THE INVENTION

Figure 1:
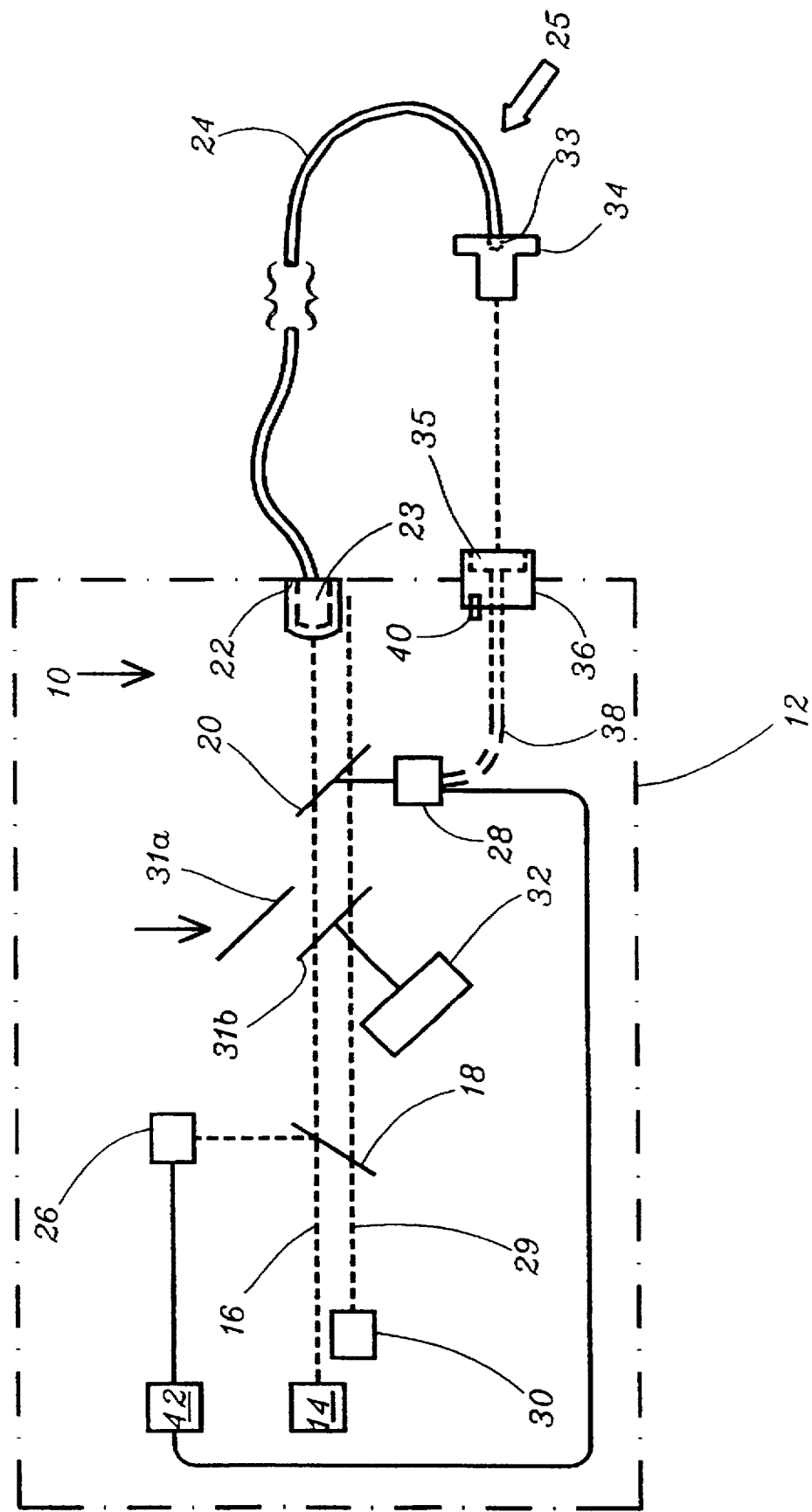
FIG. 1 is a block schematic diagram of a laser calibration device of this invention incorporated in a laser surgical system.

The following detailed description illustrates the invention by way of example, not by way of limitation of the principles of the invention. The best presently known mode for carrying out the invention is a fiber optics calibration device incorporated into a laser surgical system. The fiber optics calibration system of this invention is depicted in a block schematic diagram in the view of FIG. 1, and is depicted therein by the general reference character 10. The best presently known embodiment 10 of the present invention is incorporated into an otherwise conventional laser surgical system 12.

The laser surgical system 12 has a laser light source 14. Actually, as presently embodied by the inventors, the laser surgical system 12 has two separate laser light sources (not shown) arranged such that one or the other, but not both, may be selected for use at any given time. However, since this aspect of the embodiment is not essential to the present invention, for the sake of clarity these are being depicted herein as the unitary laser light source 14.

A light beam 16 is projected from the laser light source 14 through a first beam splitter 18, a second beam splitter 20, and into an output port 22. The output port 22 couples the light beam 16 into the fiber optic cable portion 24 of a delivery device 25 (also called a "probe") via coupling 23. The fiber optic cable 24 is a conventional device for transmitting light to a laser handpiece (not shown) or other device or tip which may be used for delivering laser energy to a treatment site.

The output port is preferably a safety port having means for recognition of unique signature elements of the coupling 23 such as disclosed and claimed in U.S. Pat. No. 4,722,337, which is hereby incorporated by reference. These signature safety and recognition elements play an important function in the safety of laser surgery procedures, e.g., insuring that the correct fiber or correct delivery device is inserted properly in the correct port of the laser console for which it is designed. Optical fibers and delivery devices are cleared by the FDA for single use only for a variety of self-evident reasons, inter alia, use may result in degradation of performance or non-sterile conditions. Further, immunological contamination may arise upon reuse of fibers and such can persist even though attempts at sterilization, particularly by untrained or inexperienced clinic or hospital personnel. Thus, the use of signature ports and connectors mounted integrally on the distal end of the fiber optic delivery device fibers helps prevent liability events from arising through the reuse of fibers, or by switching of fibers, e.g. use of unapproved connectors or adaptors, to fibers other than for which the console has been designed.

The first beam splitter 18 and the second beam splitter 20 are anti-reflection coated beam splitters designed such that approximately 1% of laser light striking each of the beam splitters 18 and 20 will be reflected therefrom. (Note that more than 1% of light would generally be reflected from an untreated surface.) A radiation detector 26 is positioned such that light reflected from the first beam splitter 18 is directed there-onto. The radiation detector 26 (sometimes referred to as a "surgical" detector) is a primary detector used for regulating and/or verifying the amount of power which is to be output from the laser surgical system 12.

A safety detector 28 is positioned such that light reflected from the second beam splitter 20 is directed thereunto. The safety detector 28, as the name implies, is provided to detect overload conditions, and the like, which might occur, for example, should the radiation detector 26 malfunction. An aiming beam 29 is a relatively low power light beam produced by an aiming beam light source 30, and which traverses the path just described in relation to the (main) light beam 16. The prior art purpose of the aiming beam 29, which purpose is also relevant to the present invention, is to allow a practitioner to see where any utensil attached to the fiber optic cable 24 is pointed, even when the laser light energy beam 16 is not on. Another purpose of the aiming beam 16 which is unique to the present invention will be discussed in further detail hereinafter.

When the safety detector 28 detects excessive power, or other such condition, a mirrored safety shutter 31a is closed such that the light beam 16 is redirected toward a light absorbing block 32, e.g. by moving to position 31b. The light block 32 stops the light beam 16 from being delivered via port 22 to the delivery device 25. The block 32 absorbs the energy of the light beam 16 when the light beam 16 is directed by the safety shutter 31 onto it.

In order to calibrate the laser surgical system 12 to account for variations in different iterations of the fiber optic cable 24, a calibration attachment 34 is attached at the distal end of the fiber optic cable 24. The calibration attachment 34 attaches over or in place of, and in like manner to, a laser handpiece (not shown) or other application delivery tip which is attached at the distal end of the fiber optic cable 24 during normal operation, as opposed to during calibration. The calibration attachment 34 of this invention preferably includes safety features. In one embodiment the safety features comprise a unique shape mateable with both the particular delivery device tip 33 and a receiver 35 of a complementary calibration receptacle 36. This signature calibration connector 34 serves a safety function similar to the signature connector 23 described above. While the safety calibration connector 34 is typically a separate piece removably engageable with both the tip 33 and the calibration port 36, it may be integral with calibration port 36, or may employ a suitable latching system, such as keyways or bayonet pin(s) and slot(s). The safety features may include electronic/electrical resistive system of the type shown in U.S. Pat. No. 4,722,337 and/or the safety switch 40 (described below). The connector 34 is thus interlockably engageable/disengageable with the port 36 and/or recognized by the console. Only when the connector is in place and the console "recognizes" the fiber will it emit the laser light beam of the proper type and/or intensity for the fiber, e.g. for calibration, for target spotting, or for treatment or surgery. Conventional external calibration devices specifically need not be used in accordance with the present invention.

To calibrate the laser surgical system 12, the calibration attachment or fitting 34 is inserted into the complementary calibration receptacle 36 (input port or calibration port). A highly efficient light pipe 38 conducts light from the calibration receptacle 36 to the safety detector 28. An electrical calibration safety switch 40 is provided within the calibration receptacle 36 such that the calibration switch 40 is closed when the calibration attachment 34 is fully inserted into and mated with the calibration receptacle 36.

In the best presently known embodiment 10 of the present invention, when the calibration switch 40 is closed, the following events occur sequentially: With the safety shutter 31 closed (in position 31b) and the laser light source 14 set to deliver a predetermined calibration power level (generally approximately 100 mW, although this value will vary depending upon the application of the invention) the practitioner inserts the calibration attachment 34 into the calibration receptacle 34 thereby depressing the calibration switch 40. This will cause the laser light source 14 to temporarily turn off, the safety shutter 31 to open, and the aiming beam light source 30 to turn on. Then, if and only if the aiming beam 29 is detected at the safety detector 28, the safety shutter 31 is opened (moved, e.g. to position 31a), and then temporarily disabled such that the safety shutter 31 will not interfere with the path of the light beam 16 when a much higher than "normal" light level is detected at the safety detector 28 (as occurs during calibration as described herein).

While it is within the scope of the present invention to practice the invention without this sequence of events just recited, it is a primary advantage of the present inventive improved fiber optics calibration device 10 that, when operated as described herein, the laser surgical system 12 will not inadvertently go into a calibration mode and thereby emit the high power light beam 16 unless the fiber optic cable 24 is properly affixed to the laser surgical system 12 at both ends of the fiber optic cable 24.

As can be appreciated in view of the above discussion, and as illustrated by FIG. 1, when the calibration attachment 34 is inserted into the calibration receptacle 36 and the laser light source 14 is activated, the total amount of light reaching the safety detector 28 will be the sum of: (a) the light initially reflected from the second beam splitter 20, and (b) the light directed through the fiber optic cable 24 and returned through the light pipe 38 to the safety detector 28. Since, as previously discussed herein, the light initially reflected from the second beam splitter 20 will be only approximately 1% of that which strikes the second beam splitter 20, and further since the efficiency of the fiber optic cable 24 typically will be approximately 85%, the amount of light which is returned through the light pipe 38 to the safety detector 28 will be more than 80 times greater than the amount of light initially reflected from the second beam splitter 20. Therefore, any calibration error introduced by the fact that the portion of the light striking the safety detector 28 after being reflected from the second beam splitter 20 will not vary as a function of the efficiency of the fiber optic cable 24. By use of the system of the invention this calibration error can be considered negligible.

It should be noted that, according to the present invention when practiced in conjunction with the safety shutter 31 as shown and described herein as being a part of the best presently known embodiment 10 of the present invention, the safety shutter 31 has to be locked out during a calibration procedure. As has been previously discussed briefly herein, since the safety detector 28 will be detecting much higher laser energy levels than it would during normal operations, and were the safety shutter 31 not locked out, it would close and the procedure as discussed hereinafter would not be possible. The calibration switch 40 is placed well within the calibration receptacle 36 such that the calibration switch 40 cannot readily be activated except when the calibration attachment 34 is inserted into the calibration receptacle 36, thus helping to insure that there will be no inadvertent lockout of the safety shutter 31 except during the actual calibration of the laser surgical system 12.

Figure 2:
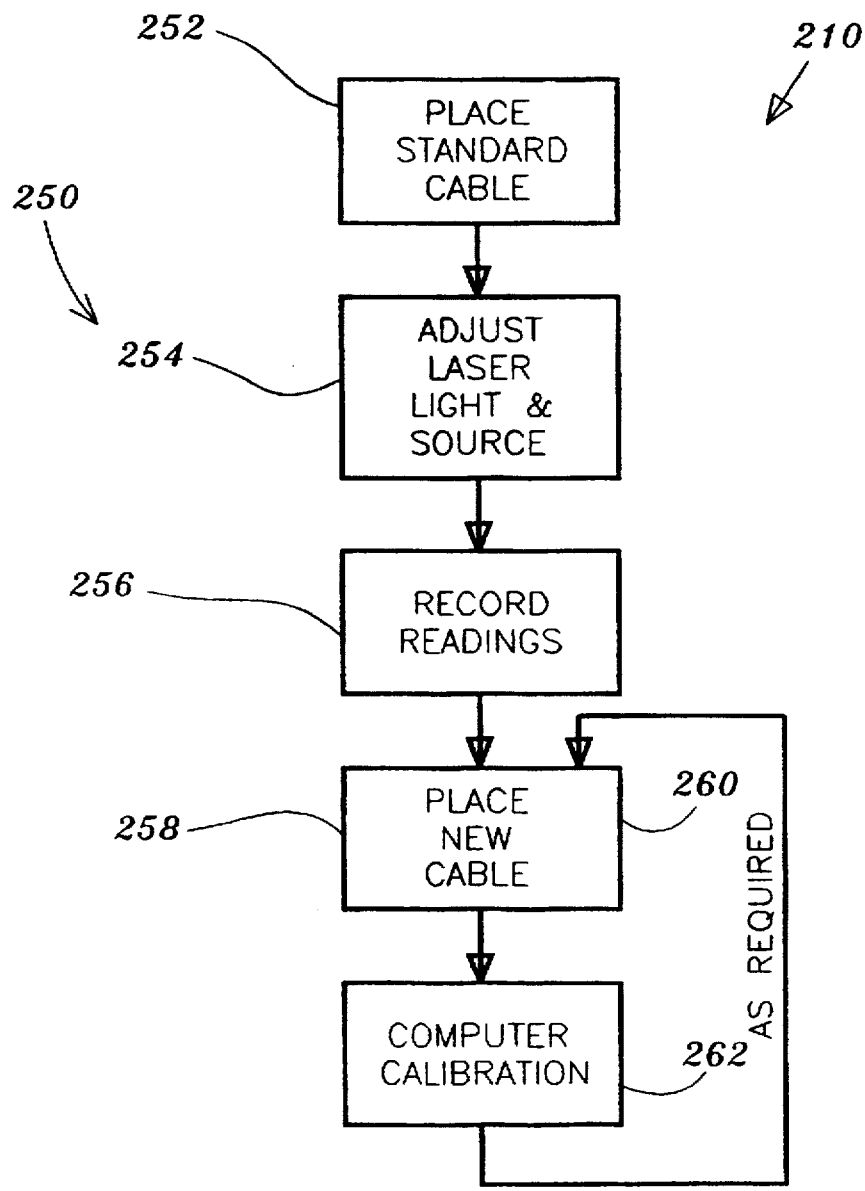
FIG. 2 is a flow chart depicting a calibration method according to the present invention.

One skilled in the art will recognize that in a modern medical laser, such as the laser surgical system 12, many or most of the functions thereof, such as sequential operations discussed herein, are controlled by a controlling computer or microprocessor 42. FIG. 2 is a flow diagram of a calibration method 210 according to the present invention. In an initial calibration procedure 250, the fiber optic cable 24 is a standard cable having a known efficiency. As previously touched upon herein, in the best presently known embodiment 10 of the present invention, the fiber optic cable 24 has an efficiency of approximately 85%, although this "standard" or "typical" value is not necessary for the practice of the present invention.

The initial calibration procedure 250 is intended to be accomplished only during initial manufacture and setup of the laser surgical system 12, or during a major overhaul and refurbishment thereof, and will generally only be accomplished by authorized manufacturing and/or service personnel. To accomplish the initial calibration procedure 250, in a "place standard cable" operation 252 the signature safety connector end 23 of the fiber optic cable 24 (having a known efficiency, as previously discussed) is inserted in recognition output port 32 of the laser surgical system 12 and the calibration safety connector 34 is attached to the distal end 33. The calibration connector 34 is then inserted into the calibration receptacle 36 engaging safety switch 40. In an "adjust laser light source" operation 24, the output of the laser light source 14 is then adjusted until a desired value is obtained at the safety detector 28. Radiation detector 26 is also detecting output. According to the best presently known embodiment of the inventive initial calibration procedure 250, this adjust operation is accomplished manually, typically by "tweaking" a potentiometer controlling an output gain stage of the laser light source 14. In a "record readings operation" 256, readings of the radiation detector 26 and the safety detector 28 are recorded for future use in the controlling computer 42. These readings may be correlated, if desired, to the particular type of cable or delivery device, data regarding which is either recognized from the signature connector 23 or manually entered in the computer if no signature connector is used. This completes the initial calibration procedure 250.

Thereafter from time to time, and particularly when a new or different fiber optic cable or delivery device 24 is attached to the laser surgical system 12 for use therewith, a "field calibration procedure" 258 will be accomplished. In a "place new cable operation" 260, the fiber optic cable 24 (having an unknown efficiency value) is engaged in the ports 22 and 36 via connectors 23 and 35 in preparation for calibration as previously discussed herein in relation to the place standard cable operation 252. Thereafter, in a computer calibration operation 262, the controlling computer 42 will note any difference between an expected reading as recorded in the record readings operation 256 and the actual present reading at the safety detector 28. When the laser surgical system 12 is operated thereafter, in accordance with normal operational procedures, the controlling computer 42 will compensate for any such difference by adjusting the output of the laser light source 14.

Various modifications may be made to the invention without altering its value or scope. For example, the light pipe 38 could be replaced by a less efficient light transmission means, such as another fiber optic cable, with appropriate compensation for any loss occurred therein being made by the controlling computer 42. Another alternative is for the controlling computer 42 to control a light transmission efficiency varying means, rather than the laser light source 14 in order to accomplish the computer calibration operation 262.

Industrial Applicability

The inventive fiber optics calibration device 10 is intended to be widely used the calibration of laser surgical devices and in other applications wherein it is necessary to calibrate fiber optic laser transmission means such that compensation can be made for losses within such transmission means.

Although it may not be strictly necessary to perform a recalibration every time the laser surgical system 12 is used in a procedure, it is anticipated that the practitioner, an assistant or laser technician, will usually perform the field calibration procedure 258 each time the laser surgical system 12 is activated for use, or at least upon some other such schedule or routine which will assure that the field calibration procedure 258 is frequently accomplished. The present invention does not affect the question of how often such calibration procedures should be performed. Rather, it is believed by the inventors that the fact that no additional apparatus is required (as compared to a separate calibration fixture in the prior art) and no switches need to be set by the operator (the calibration switch 40 is automatically set upon insertion of the calibration attachment 34 into the complementary calibration receptacle 36) such calibration procedure will, as a practical matter, actually be performed according to a predetermined schedule or routine. Therefore, it is anticipated that, in addition to reducing manufacturing cost, eliminating potential liability-generating error sources, and reducing effort on the part of the practitioner, the present inventive fiber optics calibration system 10 will result in a significant increase in the actual calibration status of medical lasers in the field.

Since the improved fiber optics calibration device 10 of the present invention may be readily produced and integrated as original equipment or retrofit kits into existing laser surgery systems and other systems wherein it is necessary or desirable to accurately calibrate a fiber optic conductor in order to compensate for losses therein, it is expected that it will be readily accepted in the industry. For these and other reasons, it is expected that the utility and industrial applicability of the invention will be both significant in scope and long-lasting in duration.

All of the above are only some of the examples of available embodiments of the present invention. Those skilled in the art will readily observe that numerous other modifications and alterations may be made without departing from the spirit and scope of the invention. Accordingly, the above disclosure is not intended as limiting and the appended claims are to be interpreted as encompassing the entire scope of the invention.

We claim:

1. A laser calibration system for a medical laser, the medical laser having a radiation detector for assisting in setting output levels of a laser light source and a safety detector for detecting overload conditions, the laser calibration system comprising:

(a) an output port affixed to the medical laser;
   (b) an optical fiber removably attachable to the output port for transmitting the output of the medical laser therethrough;
   (c) an input port for accepting the output of the fiber optic cable back into the medical laser;
   (d) a light transmission means for transmitting the output of the fiber optic cable from the input port to a calibration detector;
   (e) a beam splitter disposed to direct a portion of the output of the laser light source to the safety detector;
   (f) during calibration the safety detector records readings which are in substantial excess of the readings at the safety detector during normal operation of the medical laser;
   (g) said safety detector includes a safety shutter; and
   (h) means for preventing said safety shutter from operating during calibration such that operation of the medical laser will not be terminated due to the substantially higher readings obtained by the safety detector during calibration.

2. A laser calibration system for a medical laser, the medical laser having a radiation detector for assisting in setting output levels of a laser light source and a safety detector for detecting overload conditions, the laser calibration system comprising:

(a) an output port affixed to the medical laser;
   (b) an optical fiber removably attachable to the output port for transmitting the output of the medical laser therethrough;
   (c) an input port for accepting the output of the fiber optic cable back into the medical laser;
   (d) a light transmission means for transmitting the output of the fiber optic cable from the input port to a calibration detector; and
   (e) a controlling computer for adjusting the laser light source to account for differences in the fiber optic cable, or in the readings of said safety detector during calibration.

3. A method for calibrating a laser having a first detector for controlling the output level of a laser source and a second detector for detecting hazardous high level conditions, the method comprising:

(a) directing the output of the laser back to the second detector and recording a reading at the second detector; and
   (b) adjusting the output of the laser source according to the reading obtained at the second detector.

4. The method of claim 3, wherein:

(a) the laser is a medical laser unit for laser surgery and therapy.

5. The method of claim 3, wherein:

(a) the laser includes a safety shutter which blocks the output of the laser; and
   (b) the safety shutter is prevented from operating while the laser is being calibrated.

6. The method of claim 3, wherein:

(a) a light pipe is used to complete the path of the output of the laser back to the second detector.

7. The method of claim 6, wherein:

(a) the light pipe transfers light from a calibration receptacle on the laser to the second detector.

8. The method of claim 7, wherein:

(a) a fiber optic cable transfers light from the output of the laser to the calibration receptacle.

9. The method of claim 8, wherein:

(a) a calibration fitting is attached to the distal end of the fiber optic cable during calibration, and
   (b) the calibration fitting is inserted into the calibration receptacle such that light is transferred from the fiber optic cable to the light pipe.

10. The method of claim 9, wherein:

(a) an electrical switch within the calibration receptacle is activated when the calibration fitting is inserted into the calibration receptacle.

11. The method of claim 10, wherein:

(a) the electrical switch prevents operation of a safety shutter such that the output of the laser is not blocked by the safety shutter even though the second detector detects a light level that would otherwise indicate an overload condition.

12. A laser calibration system for a medical laser, the medical laser having a radiation detector for assisting in setting output levels of a laser light source and a safety detector for detecting overload conditions, the laser calibration system comprising:

(a) an output port affixed to the medical laser;
    (b) an optical fiber removably attachable to the output port for transmitting the output of the medical laser therethrough;
    (c) an input port for accepting the output of the fiber optic cable back into the medical laser;
    (d) a light transmission means for transmitting the output of the fiber optic cable from the input port to a calibration detector; and
    (e) an aiming beam light source for producing an aiming beam into the fiber optic lead.

13. The laser calibration system of claim 12, and further including:

(a) a calibration attachment affixed to the distal end of the fiber optic cable, the calibration attachment being adapted for insertion into the input port and triggering a safety switch disposed in association with said input port.

14. The laser calibration system of claim 12, wherein;

(a) the light transmission means is a light pipe.

15. The laser calibration system of claim 12, wherein:

(a) the calibration detector is the safety detector.

16. The laser calibration system of claim 12, wherein:

(a) operation of the medical laser is prevented during calibration unless a safety switch is depressed and the aiming beam is detected at the safety detector.

17. The laser calibration system of claim 16, wherein:

(a) a safety shutter interferes with the output of the medical laser to prevent operation of the medical laser.

* * * * *